United States Patent [19]

Curtis-Prior et al.

[11] Patent Number: 4,795,761

[45] Date of Patent: Jan. 3, 1989

[54] CONTRACEPTIVE COMPOSITION

[75] Inventors: Peter B. Curtis-Prior, Histon; Stewart T. Leslie, Cambridge, both of United Kingdom; Ronald B. Miller, Basel, Switzerland; Alison L. Shill, Histon, United Kingdom

[73] Assignee: Euroceltique S.A., Luxembourg, Luxembourg

[21] Appl. No.: 22,670

[22] Filed: Mar. 6, 1987

[30] Foreign Application Priority Data

Mar. 12, 1986 [GB] United Kingdom ............... 8606132
Mar. 26, 1986 [GB] United Kingdom ............... 8607569

[51] Int. Cl.$^4$ ................................. A61K 31/135
[52] U.S. Cl. .................... 514/652; 514/236.2; 514/415; 514/613; 514/650; 514/718; 514/843
[58] Field of Search ............. 424/DIG. 14, DIG. 15; 514/841–843, 415, 237, 613, 650, 652, 718

[56] References Cited

U.S. PATENT DOCUMENTS 4,277,461 7/1981 Lücker et al. ............ 424/DIG. 14
4,384,003 5/1983 Kazmiroski et al. ............... 514/718
4,575,558 3/1986 Mai et al. ........................... 549/453

OTHER PUBLICATIONS

S. M. Louis, A Comparison of the Effects of Nonoxynol-9 and Chlorhexidine on Sperm Motility, Contraception, vol. 32, No. 2, 1985, pp. 199–205.

K. Rajkumar et al., Effect of Some Adrenergic Drugs on Fertility in Rats—A Preliminary Communication, Indian J. Med. Res. 67, 1978, pp. 478–481.

*Primary Examiner*—Leonard Schenkman
*Attorney, Agent, or Firm*—Steinberg & Raskin

[57] ABSTRACT

A contraceptive composition for application to the vagina of a female mammal comprising a contraceptive amount of a contraceptive combination, the combination containing a spermicidal or sperm-immobilizing polyethoxyethanol and a beta-adrenergic blocker (as herein before defined).

The polyethoxyethanol may be, for example, an octoxynol or, which is preferred, a nonoxynol, especially nonoxynol-9. The beta-adrenergic blocker is preferably a spermicidal or sperm-immobilizing beta-adrenergic blocker, propranolol (in particular the d-isomer) being especially preferred.

The composition may also contain a spermicidal or sperm-immobilizing preservative.

10 Claims, No Drawings

CONTRACEPTIVE COMPOSITION

The present invention relates to a contraceptive composition to be applied to the vagina of a female mammal, especially a human female, and to a contraceptive method employing the composition.

According to the present invention, there is provided a contraceptive composition for application to the vagina of a female mammal comprising a contraceptive amount of a contraceptive combination, the combination comprising at least one spermicidal or sperm-immobilising polyethoxyethanol and at least one beta-adrenergic blocker (as herein after defined).

"A beta-adrenergic blocker" is a beta-adrenoceptor antagonist, that is, a substance which acts as a competitive inhibitor of the effects of catecholamines at beta-adrenergic receptor sites. A beta-adrenergic blocker, according to the present invention, must also have, in combination with a spermicidal or sperm immobilising polyethoxyethanol, a synergistic (rather than an additive) effect on the inhibition of the motility of human sperm.

Preferably the beta-adrenergic blocker is a spermicidal or sperm-immobilising material.

In the present specification, a polyethoxyethanol or a beta-adrenergic blocker is "spermicidal or sperm-immobilising" if it reduces sperm motility to 50% of its original level ($IC_{50}$) at a concentration of 50 mmolar or less, preferably at a concentration or 25 mmolar or less, most preferably at a concentration of 10 mmolar or less.

The at least one beta-adrenergic blocker may or may not be optically active. However, if it is optically active, then, in the present specification, the phrase "beta-adrenergic blocker" incorporates
(a) a mixture of the optical isomers,
(b) the pure optical isomer having the higher cardiovascular activity, and
(c) the pure optical isomer having the lower (in some cases no) cardiovascular activity.

In one preferred embodiment of the present composition, the beta-adrenergic blocker is chosen from acebutolol, alprenolol, bufuralol, metoprolol, oxprenolol, penbutolol, pindolol, propranolol and timolol, with alprenolol, bufuralol, penbutolol and propranolol being most preferred and propranolol the most preferred.

In another preferred embodiment of the present composition, the beta-adrenergic blocker exhibits non-specific membrane activity (as defined by H. J. Smith, J. Mol. Cell. Cardiol, 1982, 14, 495). Suitable materials include acebutolol, alprenolol, bufuralol, bunolol, oxprenolol, penbutolol, pindolol, pronethalol, propranolol, timolol and toliprolol, with acebutolol, alprenolol, bufuralol, oxprenolol, penbutolol, pindolol and propranolol being particularly preferred.

In yet another preferred embodiment of the present composition, the beta-adrenergic blocker exhibits non-specific membrane activity and has an apparent octanol/buffer (pH 7.4) partition coefficient (as measured by the method of P. H. Hinderling et al, J. Pharmacokinetics Biopharmaceutics, 1984, 12, 263) of greater than 1. Suitable materials include alprenolol, bufuralol, penbutolol and propranolol, with propranolol being particularly preferred.

As mentioned above, the beta-adrenergic blocker may or may not be optically active. If it is however, it is preferred that the present composition contains the optical isomer having the lower cardiovascular activity in equal or greater proportion to the optical isomer having the higher cardiovascular activity. For example, when penbutolol is the chosen beta-blocker, the composition would preferably contain (as a proportion of the penbutolol) 50% or more (by wt) of d-penbutolol. Similarly, when propranolol is the beta-blocker, the composition would preferably contain (as a proportion of the propranolol) 50% or more (by wt) of d-propranolol.

In a particularly preferred embodiment of this invention the composition contains (as a proportion of the beta-blocker component) at least 90% (by wt), especially at least 99% (by wt) of at least one optical isomer of at least one beta blocker according to this invention, wherein the at least one optical isomer has little or no cardiovascular activity. Examples of such optical isomers include d-penbutolol and d-propranolol, with d-propranolol being particularly preferred.

The at least one spermicidal or sperm-immobilising polyethoxyethanol preferably has the following formula,

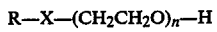

$$R-X-(CH_2CH_2O)_n-H$$

in which R is an alkyl, alkenyl or aralkyl group having from 5 to 20 carbon atoms, X is —O— or —CONH— and n has a value of 3 to 20. It should be noted that, in the present specification, the value quoted for n in the formulae of polyethoxyethanols represents an average value of the number of oxyethylene groups present in the polyoxyethylene chain, for a given type of polyethoxyethanol. Thus, nonoxynol-9 contains an average of nine oxyethylene groups in the polyoxyethylene chain.

Thus the polyethoxyethanol may be an N-hydroxyethylpolyoxyethyl carboxylic acid amide of the type described in U.S. Pat. No. 4,277,461. Alternatively, and preferably, the polyethoxyethanol may be an alkylphenoxy polyethoxyethanol of the type described in U.S. Pat. No. 2,889,250.

In a particularly preferred embodiment of the present composition, the spermicidal or sperm-immobilising polyethoxyethanol has the formula

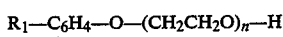

$$R_1-C_6H_4-O-(CH_2CH_2O)_n-H$$

wherein n has a value of 3 to 15, especially of 5 to 11 and R is an alkyl group, preferably containing from 8 to 10 carbon atoms. The most preferred materials of this type are known as the octoxynols (wherein $R_1$ is a $C_8$ alkyl group) and nonoxynols (wherein $R_1$ is a $C_9$ alkyl group), with the nonoxynols (3 to 15, especially 5 to 11) being most especially preferred.

The present contraceptive composition may be in any form suitable for application to the vagina. For example, the composition may be in the form of a pessary, sponge, cream, liquid douche, gel, jelly, aerosol foam, impregnated tampon or a controlled delivery device. Alternatively, the composition may be used as the lubricant on a condom, cap diaphragm, etc.

The amount of the active constituents present in a unit dose of the present composition must be sufficient, in combination, to produce a contraceptive effect. Generally, this means that the contraceptive use of the present composition must produce a Pearl index of 4 or less, preferably 3 or less, most preferably 2 or less. (N.B. The Pearl Index is the number of unwanted pregnancies which occur in 100 women using a particular contraceptive method for one year). In the case of a lubricated condom, the amount of present composition present on the condom must be such that the combined contraceptive effect of the condom and the present composition should produce a Pearl Index of 4 or less, preferably 3 or less, most preferably 2 or less.

The amount of beta-adrenergic blocker present in a unit dose of the present composition is preferably insufficient to produce more than a 10% change (from baseline) in the blood-pressure and/or heart-rate of a subject, upon vaginal administration of the unit dose.

Preferably a unit dose of the present composition contains between 0.0025 and 0.5 mmoles, especially between 0.0025 and 0.25 mmoles, most especially between 0.0025 and 0.025 mmoles, of the polyethoxyethanol and between 0.002 and 0.1 mmoles, especially beween 0.004 and 0.05 mmoles, most especially between 0.004 and 0.025 mmoles of the beta-adrenergic blocker. In a particularly preferred embodiment of this invention, a unit dose of the composition contains between 1.54 and 308 mg, especially between 1.54 and 154 mg, most especially 1.54 and 15.4 mg of Nonoxynol-9 and between 0.52 and 26 mg, especially between 1.04 and 13 mg, most especially between 1.04 and 6.5 mg of d-propranolol.

The present contraceptive composition may be compounded into a suitable dosage form by procedures that are conventional in the pharmaceutical art, by employing the usual excipients (buffer, emulsifier, preservative, etc.), the choice and amount of which will be apparent to those skilled in the art.

For example, a pessary may be prepared by mixing the active constituents with at least one polyethylene glycol, the glycol or mixture of glycols having a melting point at or below body temperature. In order to facilitate the efficient dispersion of the active ingredients in the vagina, the pessary may also contain foam producing substances, such as sodium bicarbonate and sodium phosphate, and, in order to assure long duration of the foam, a foam stabilising substance, such as sodium lauryl sulphate.

Alternatively, a contraceptive sponge may be prepared by absorbing the active constituents into a biocompatible, bioinsoluble, non-toxic sponge-like soft polymer. Suitable polymers for this use are well known in the art, for example 2-hydroxyethyl methacrylate. In another embodiment of the present invention, a controlled delivery device consists of the active constituents absorbed in a biocompatible, bioinsoluble, flexible, silicone rubber matrix, especially a dimethylpolysiloxane.

A contraceptive cream according to this invention may contain a hydrocarbon base (e.g. white petrolatum), a solvent (e.g. glycerin or propylene glycol) and an emulsifier (e.g. cetyl alcohol, stearyl alcohol, sodium lauryl sulphate). A contraceptive jelly may contain a solvent (e.g. glycerin or propylene glycol) a gel forming agent (e.g. sodium alginate (especially with calcium ions), tragacanth, gelatin, methyl cellulose, sodium carboxymethylcellulose, carbomer and polyvinyl alcohol) and a preservative (e.g. methyl p-hydroxybenzoate). A contraceptive foam may contain a fluorinated hydrocarbon propellant and a surfactant or emulsifier.

In a particularly preferred embodiment of the present composition, the composition contains at least one preservative that is itself spermicidal or sperm-immobilising, that is it reduces sperm motility by 50% at concentrations of 50 mmolar or less, preferably at concentrations of 25 mmolar or less, most preferably at concentrations of 10 mmolar or less. Suitable materials are bronopol, benzalkonium chloride, benzethonium chloride, chlorhexidine and hydroxybenzoate esters.

According to a still further aspect of the present invention, there is provided a process for the preparation of a contraceptive composition for application to the vagina of a female mammal comprising combining at least one spermicidal or sperm-immobilising polyethoxyethanol and at least one beta-adrenergic blocker (as herein before defined) to form a contraceptive amount of a contraceptive combination.

The present inventors have surprisingly found that the addition of a beta-adrenergic blocker according to this invention (especially d-propranolol) to a spermicidal or sperm-immobilising polyethoxyethanol has a synergistic (rather than an additive) effect on the inhibition of the motility of human sperm. In particular, and most surprisingly, the inventors have found that low levels of the beta-blocker, levels that, in isolation, have only a moderate effect on sperm motility, exercise in combination with the polyethoxyethanol, a dramatic control over sperm motility.

The present contraceptive composition, together with evidence of its spermicidal or sperm-immobilising properties, is illustrated in the following Examples.

MATERIALS AND METHODS

Measurements of Human Sperm Motility

A simple method for measuring human sperm motility was developed as a modification to the method of C. Y. Hong et al, *Br. J. Clin. Pharm.*, 1981, 11, 385. The method used two chambers separated by a membrane and assessed the proportion of spermatozoa, from a small aliquot of semen, that moved across the membrane from the upper to the lower chamber.

Materials a. Nuclepore (Trade Mark) polycarbonate membrane filters (13 mm×5 um; Sterilin).
b. Silated 10 ml glass vials.
c. 2 ml Sabre (Trade Mark) disposable plastic syringes. (Philip Harris Medical Ltd.)
d. Phosphate buffered saline (pH 7.3, Dulbecco A (Trade Mark); Oxoid.
e. 10% Formalin solution.
f. Haemocytometers—improved Neubauer (Trade Mark).
g. Semen sample, to be used within 4 hours of collection.

Method

The apparatus consisted of an upper and a lower chamber, the upper chamber being the plunger of a 2 ml disposable syringe. A 13 mm diameter Nuclepore membrane filter was bonded to the plunger using dichloromethane.

Aliquots of fresh human semen were mixed, in a 2 to 1 volume ratio, with either phosphate buffered saline (pH 7.3) or a phosphate buffered saline solution of nonoxynol-9, d-propranolol or a mixture of nonoxynol-9 and d-propranolol (pH 7.3). The mixture was pre-incubated at 37° C. for 10 minutes.

After pre-incubation the mixture was vortexed and 100 μl was pipetted onto the membrane of the upper chamber. The upper chamber was then inserted into the lower chamber, which contained 2 ml of phosphate buffered saline at 37° C.

The relative positions of the two chambers were fixed so that the fluid levels were equal.

The apparatus was then incubated for 90 mins. at 37° C. After this time, the upper chamber was removed and its contents were washed into 1.9 ml phosphate buffered saline containing 50 ul of 10% formalin solution by breaking the membrane. The spermatozoa in the lower chamber were also killed by adding 50 ul of the formalin to the lower chamber.

Finally, the number of spermatozoa in the upper and lower chambers were counted using a haemocytometer. The proportion of spermatozoa that traverse the membrane into the lower chamber is referred to as the trans-membrane migration ratio.

The control of sperm motility achieved by nonoxynol-9, d-propranolol and mixtures of nonoxynol-9 and d-propranolol is given in Table 1, as a % of a control experiment (control 0% inhibition). mM represents millimolar.

TABLE 1

Effect of Nonoxynol-9 and d-Propranolol on Sperm Motility

| | % Inhibition of Sperm Motility |
|---|---|
| Control | 0 |
| Nonoxynol-9 (conc. 0.16 mM) | 12.5 |
| Nonoxynol-9 (1.6 mM) | 97.7 |
| d-Propranolol (1.0 mM) | 28.0 |
| d-Propranolol (2.5 mM) | 76.5 |
| Nonoxynol-9 (0.16 mM) and d-Propranolol (1.0 mM) | 62.4 |
| Nonoxynol-9 (1.6 mM) and d-Propranolol (1.0 mM) | 99.04 |
| Nonoxynol-9 (0.16 mM) and d-Propranolol (2.5 mM) | 98.0 |
| Nonoxynol-9 (1.6 mM) and d-Propranolol (2.5 mM) | 99.94 |

Using the same technique, but a different sperm source the control of sperm motility achieved by nonoxynol-9, various beta-blockers and mixtures of nonoxynol-9 and a beta-blocker was measured. Results given in Table 2, as a % of a control experiment (control=0% inhibition). Again, mM represents millimolar. $IC_{50}$ is the concentration of nonoxynol-9 that gave 50% inhibition of sperm motility.

TABLE 2

Effect of Nonoxynol-9 and Various Beta-Blockers on Sperm Motility

| | % Inhibition of Sperm Motility |
|---|---|
| Control | 0 |
| Nonoxynol-9 ($IC_{50}$) | 50 |
| d-Propranolol (1.0 mM) | 3.6 |
| Nonoxynol-9 ($IC_{50}$) and d-Propranolol (1.0 mM) | 100.0 |
| d,1-Propranolol (1.0 mM) | 24.6 |
| Nonoxynol-9 ($IC_{50}$) and d,1-Propranolol (1.0 mM) | 97.7 |
| Penbutolol (0.1 mM) | 6.2 |
| Nonoxynol-9 ($IC_{50}$) and Penbutolol (0.1 mM) | 97.8 |
| Bufuralol (1.0 mM) | 28.5 |
| Nonoxynol-9 ($IC_{50}$) and Bufuralol (1.0 mM) | 97.7 |
| 1-Alprenolol (1.0 mM) | 17.0 |
| Nonoxynol-9 ($IC_{50}$) and 1-Alpenolol (1.0 mM) | 99.0 |
| Oxprenolol (5.0 mM) | 3.4 |
| Nonoxynol-9 ($IC_{50}$) and Oxprenolol (5.0 mM) | 98.9 |
| Metoprolol (10.0 mM) | 7.1 |
| Nonoxynol-9 ($IC_{50}$) and Metoprolol (10.0 mM) | 99.5 |

The results of further tests, using yet another source of sperm are given in Table 3. mM represent millimolar. $IC_{50}$ is again the concentration of nonoxynol-9 that gave 50% inhibition of sperm motility.

TABLE 3

Effect of Nonoxynol-9 and Various Beta-Blockers

| | % Inhibition of Sperm Motility |
|---|---|
| Control | 0 |
| Nonoxynol-9 ($IC_{50}$) | 50.0 |
| d-Propranolol (1.0 mM) | 4.0 |
| Nonoxynol-9 ($IC_{50}$) and d-Propranolol (1.0 mM) | 100.0 |
| Penbutolol (0.1 mM) | 0.0 |
| Nonoxynol-9 ($IC_{50}$) and Penbutolol (0.1 mM) | 98.0 |
| Bufuralol (1.0 mM) | 22.0 |
| Nonoxynol-9 ($IC_{50}$) and Bufuralol (1.0 mM) | 97.0 |
| 1-Alprenolol (1.0 mM) | 26.9 |
| Nonoxynol-9 ($IC_{50}$) and 1-Alprenolol (1.0 mM) | 100.0 |
| Oxprenolol (5 mM) | 0.0 |
| Nonoxynol-9 ($IC_{50}$) and Oxprenolol (5 mM) | 99.0 |
| Metoprolol (10 mM) | 0.0 |
| Nonoxynol-9 ($IC_{50}$) and Metoprolol (10 mM) | 100.0 |
| Pindolol (25 mM) | 10.2 |
| Nonoxynol-9 ($IC_{50}$) and Pindolol (25 mM) | 100.0 |

The results of further test, using another source of sperm are given in Table 4. mM and $IC_{50}$ have the meanings set out above.

TABLE 4

Effect of Nonoxynol-9 and Various Beta Blockers

| | % Inhibition of Sperm Motility |
|---|---|
| Control | 0 |
| Nonoxynol-9 ($IC_{50}$) | 50.0 |
| Timolol (25 mM) | 4.9 |
| Nonoxynol-9 ($IC_{50}$) and Timolol (25 mM) | 90.0 |
| Acebutolol (25 mM) | 11.3 |
| Nonoxynol-9 ($IC_{50}$) and Acebutolol (25 mM) | 98.0 |

The results of a further test, using another source of sperm are given in Table 5. mM and $IC_{50}$ have the meanings set out above.

TABLE 5

Effect of Octoxynol and Various Beta-Blockers

| | % Inhibition of Sperm Motility |
|---|---|
| Control | 0 |
| Octoxynol ($IC_{50}$) | 50.0 |
| d-Propranolol (1 mM) | 0.2 |
| Octoxynol ($IC_{50}$) and d-Propranolol (1 mM) | 90.0 |
| d,1-Propranolol (1 mM) | 10.5 |
| Octoxynol ($IC_{50}$) and d,1-Propranolol (1 mM) | 97.0 |
| Penbutolol (0.1 mM) | 17.8 |
| Octoxynol and Penbutolol (0.1 mM) | 99.0 |

What we claim is:

1. A contraceptive composition for application to the vagina of a female mammal comprising a contraceptive effective amount of a contraceptive combination, the combination comprising at least one spermacidal or sperm-immobilising polyethoxyethanol selected from the group consisting of octoxynol and nonoxynol in a spermacially effective concentration that gives up to and including about 50% of inhibition of sperm motility when used alone and at least one beta adrenergic blocker selected from the group consisting of acebutolol, alprenolol, bufuralol, penbutolol, metoprolol, pindolol, propanolol and timolol in a concentration of about 0.1 to 25 mmoles.

2. A composition according to claim 1 wherein said beta-adrenergic blocker is alprenolol, bufuralol, penbutolol or propranolol.

3. A composition according to claim 1 wherein said beta-adrenergic blocker is propranolol.

4. A composition according to claim 1 wherein said beta-adrenergic blocker is d-propranolol.

5. A composition according to claim 1 said composition containing at least two beta-adrenergic blockers in optically active form, one of said beta-adrenergic blockers having a lower cardiovascular activity than the other, the proportion of the total weight of said other optically active beta-adrenergic blocker being at least 50% of the optically active beta-adrenergic blocker having the lower cardiovascular activity.

6. A composition according to claim 5 wherein said other optically active beta-adrenergic blocker is at least 90% (by weight) of the optically active beta-adrenergic blocker having the lower cardiovascular activity.

7. A composition according to claim 5 wherein said other optically active beta-adrenergic blocker is at least 99% (by weight) of the optically active beta-adrenergic blocker having the lower cardiovascular activity.

8. A composition according to claim 1 further comprising a spermicidal or sperm-immobilising preservative selected from the group consisting of bronopol, benzalkonium, chloride, benzethonium chloride, chlorhexidine and hydroxybenzoate esters.

9. A contraceptive composition according to claim 1 in a form of a pessary, a sponge, a cream, a liquid douche, a gel, a jelly, a foam, an impregnated tampon, a controlled delivery device or a lubricant on a condom.

10. A contraceptive method which comprises applying to the vagina of a female mammal a contraceptive effective amount of the contraceptive combination of claim 1.

* * * * *